United States Patent [19]
Benaroya et al.

[11] 3,992,463
[45] Nov. 16, 1976

[54] OXYCHLORINATION OF ETHYLENE WITH A FIXED BED CATALYST

[75] Inventors: Gerard Benaroya, Bois-Colombes; Maxime Graulier, Paris; Jacques Long, Saint-Auban; Francois Laine, Martigues, all of France

[73] Assignee: Produits Chimiques PECHINEY-SAINT-GOBAIN, Paris, France

[22] Filed: Mar. 27, 1972

[21] Appl. No.: 238,692

Related U.S. Application Data

[63] Continuation of Ser. No. 730,606, May 20, 1968, abandoned.

[30] Foreign Application Priority Data

May 19, 1967 France .............................. 67.106970

[52] U.S. Cl. ........................ 260/659 A; 260/656 R
[51] Int. Cl.² ...................................... C07C 17/00
[58] Field of Search ........ 260/659 A, 662 A, 654 A, 260/658 R, 662 R

[56] References Cited
UNITED STATES PATENTS

| | | | |
|---|---|---|---|
| 3,184,515 | 5/1965 | Penner et al. | 260/659 A |
| 3,190,931 | 6/1965 | Laine et al. | 260/659 A |
| 3,363,010 | 1/1968 | Schwarzenbek | 260/659 A |
| 3,427,359 | 2/1969 | Rectenwald et al. | 260/659 A |
| 3,449,450 | 6/1969 | Bohl et al. | 260/659 A |

FOREIGN PATENTS OR APPLICATIONS

| | | | |
|---|---|---|---|
| 519,691 | 12/1955 | Canada | 260/654 H |
| 1,104,666 | 2/1968 | United Kingdom | 260/659 A |

*Primary Examiner*—Delbert E. Gantz
*Assistant Examiner*—Joseph A. Boska

[57] ABSTRACT

Oxychlorination of ethylene with hydrochloric acid and oxygen with a fixed bed catalyst subdivided into independent reaction zones whereby a substantial proportion of the ethylene is converted to 1,1,2-trichloroethane and 1,1,2,2-tetrachloroethane along with 1,2-dichloroethane.

9 Claims, No Drawings

OXYCHLORINATION OF ETHYLENE WITH A FIXED BED CATALYST

This is a continuation of application Ser. No. 730,606, filed May 20, 1968, now abandoned.

This invention relates to the oxychlorination of ethylene with a fixed bed catalyst whereby a substantial proportion of the ethylene is converted to 1,1,2-trichloroethane and 1,1,2,2-tetrachloroethane simultaneously with the formation of 1,2-dichloroethane.

It is well known that the oxychlorination of ethylene in the presence of a fixed bed catalyst yields 1,2-dichloroethane. It is also known that the oxychlorination reaction can be carried out to provide other chlorinated compounds of ethane and ethylene, such as dichloroethylenes, trichloroethylene, 1,1,2-trichloroethane and 1,1,2,2-tetrachloroethane. However, the prior art processes, especially those which make use of a single catalyst in a single reaction zone, are incapable of producing large amounts of saturated $C_2$ compounds which are more highly chlorinated than 1,2-dichloroethane without simultaneous occurrence of side reactions, such as combustion, partial oxidation of ethylene and/or dehydrochlorination reactions which yield $C_2$ unsaturated chlorinated compounds. In fact, in the hottest regions of the catalytic zone, which develop by reason of the exothermicity of the reaction, the concentration of 1,2-dichloroethane is low and reactions to form 1,1,2-trichloroethane and 1,1,2,2-tetrachloroethane are practically nil because of the lack of 1,2-dichloroethane. Besides, in the catalytic zone immediately beyond the hot zones, the concentration of the reactants 1,2-dichloroethane, hydrochloric acid and oxygen is high but the temperature is relatively low so that reaction to form 1,1,2-trichloroethane and 1,1,2,2-tetrachloroethane, which have high activation energies, develops at a slow rate.

Furthermore, the catalyst normally used in oxychlorination of ethylene gives rise to a reaction which yields essentially 1,2-dichloroethane.

It is an object of this invention to provide a process of oxychlorination of ethylene in the presence of a fixed bed catalyst wherein a substantial amount of the ethylene is converted to saturated $C_2$ compounds having an amount of chlorination higher than 1,2-dichloroethane and more particularly a reaction in which a substantial proportion of the ethylene is converted to 1,1,2-trichloroethane and 1,1,2-2-tetrachloroethane along with 1,2-dichloroethane in the product.

It is an object of this invention to provide a new process for the oxychlorination of ethylene which yields, in addition to 1,2-dichloroethane, large proportions of 1,1,2-trichloroethane and 1,1,2,2-tetrachloroethane in which the latter two compounds represent at least 8 molar per cent of the ethylene transformed and preferably 10 to 15 molar per cent and, in some instances, up to 20 molar per cent of the ethylene transformed. Such 1,1,2-trichloroethane, and 1,1,2,2-tetrachloroethane find excellent use either alone or as raw materials for the preparation of vinylidene chloride, dichloroethylenes and trichloroethylene.

The invention relates also to a new catalytic system for use in the oxychlorination of ethylene.

In accordance with the present invention, the desired improvement is achieved by subdividing the fixed bed catalyst into two zones which are connected one to the other for the successive passage of the reaction gases threthrough including the feed of ethylene, hydrochloric acid and oxygen or an oxygen-containing gas to effect part of the reaction in the first zone with the remainder in the second zone, with the second zone embodying one or more different operating conditions which are effective to impart greater reactivity, such as a higher reaction rate in the second zone by comparison with the first zone.

Such differential in operating conditions between the first and second catalyst reaction zones to increase the reactivity or rate of reaction in the second zone may be achieved in various ways, taken alone or in combination, namely: by the nature of the catalyst, the respective cross-sections of the zones, reaction temperature, feed flow rate, conversion rate of ethylene issuing from the first zone, and molecular ratios of reactants in the feed.

More specifically, one means for achieving the desired difference in behavior between the catalytic zones resides in providing means for increase in the cross-sectional area of the second zone by comparison with the first. For this purpose, both catalytic zones can be formed of one or more tubular members of multi-tubular devices in which the tubes forming the second catalytic zone have a total diameter larger than the total diameter of the tubular members of the first zone of catalyst. In the preferred practice of this concept, it is desirable to make use of a ratio greater than 1 but not more than 3 between the diameters of the tubular member of the first zone as compared to the second zone.

Another means for achieving the desired results resides in the utilization of a catalytic system in the second zone which is more active than the catalyst in the first zone. For this purpose, the carrier on which the catalyst is deposited can be selected to have a smaller average surface area in the first zone by comparison with the surface area of the carrier in the second zone. For example, the catalyst in the first zone can be in the form of a catalytic agent deposited on a carrier having an average surface area less than 3 $m^2/g$ in a pore diameter distribution of from 0.05 to 10 microns, while the catalyst in the second zone is formed of the same or different catalytic agents deposited on a carrier having an average specific surface area at least 10% greater than the average surface area of the carrier of the first zone, but preferably not exceeding 10 $m^2/g$ in a pore diameter distribution within the range of 0.05 to 10 microns.

The term "average specific surface" is used because of the fact that, if a series of samples of catalyst are taken from different parts of the catalytic bed for determination of the specific surface area of the carrier by the B.E.T. method, it will be found that the extreme values will not deviate more than 100% from the average value.

Generally, the particle size of the carrier will be within the range of 1 to 15 mm. When the tube diameter of the first and second catalyst reaction zones have similar crosssectional areas, it may be beneficial to make use of a granular size for the catalyst which is lower in the second zone than in the first, but preferably, not below 1 mm.

Temperature is another parameter which can be used effectively to achieve different reaction rates in the reaction zones. To achieve the conditions desired for variation in the reaction rate between the zones, it is desirable, in accordance with the preferred practice of this invention, to maintain a reaction temperature in the second catalytic reaction zone which is higher than the reaction temperature in the first zone, with the preferred differential being a temperature in the second reaction zone which is 5° to 50° C higher than the reaction temperature in the first zone. In the practice of this concept of the invention, the ethylene, hydrochloric acid and oxygen-containing gas are passed through the first catalytic zone for reaction at a temperature within the range of 250° to 400° C and preferably 280° to 370° C and the effluent from the first reaction zone is introduced into the second catalytic reaction zone for reaction at a temperature within the range of 255° to 410° C and preferably within the range of 285° to 400° C, but with the region of highest temperature in the second zone regulated to be about 5° to 50° C above the region of highest temperature in the first reaction zone.

While pressure is not an important variable in the process of this invention, a number of advantages are derived from operation of the described oxychlorination process at positive pressures of from 1 to 10 absolute bars and preferably within the range of 2 to 7 absolute bars. Although pressures higher than 10 absolute bars can be used, the apparatus permitting, no marked advantage is derived from operation under such higher pressures. In the preferred practice of this invention, the second catalytic reaction zone is operated at a pressure above atmospheric pressure since such positive pressures favor the formation of 1,1,2-trichloroethane and 1,1,2,2-tetrachloroethane. However, where other parameters are used for achieving the desired reaction rate, substantially equal pressures can be employed in the two zones.

In the practice of this invention, the feed of ethylene is maintained at a flow rate of 0.5 to 12 moles per hour per liter of catalyst and preferably 2 to 9 moles per hour per liter of catalyst. The total molar feed ratio of $HCl/C_2H_4$ is maintained within the range of 1.8 and 3.0 and preferably within the range of 2.1 and 2.5 and the total molar feed ratio of $O_2/C_2H_4$ is maintained within the range of 0.5 to 1.5 and preferably within the range of 0.6 to 0.8.

In accordance with one embodiment of the invention, the operating conditions are regulated so that ethylene is only partially converted in the first catalytic reaction zone with the additional conversion calculated to take place in the second catalyst reaction zone. In the preferred practice of this concept, the conditions are regulated so that 40% to 80% of the ethylene conversion occurs in the first reaction zone. This can be achieved by withholding a portion of one or more of the ingredients from the first reaction zone for later introduction with the partially reacted materials into the second catalyst reaction zone. The portion withheld can constitute up to 60 molar percent of the one or more of the reagents. By way of another ramification for achieving the desired result, it is possible to regulate the conversion rate of ethylene in the first reaction zone by relating flow rates of reagents to the first reaction zone with the temperature to appropriate values.

As the carrier for the catalyst, use can be made of one or more of the following substances which are given by way of illustration, but not by way of limitation, such as: silica, silicates, clays, alumino-silicate, magnesia, graphite, and preferably alumina. Excellent results can be obtained with a carrier formed of alumina having an average specific surface below 1 $m^2/g$ in the first zone and an average specific surface below 4 $m^2/g$ in the second catalyst zone. The catalytic agent deposited on the carrier can be the same or different for each of the catalyst reaction zones. Catalytic agents which can be used are made up essentially of at least one compound of an element in the following list, namely: alkali metals, alkaline earth metals, bismuth, cadmium, chromium, cobalt, copper, tin, iron, magnesium, manganese, nickel, platinum, rare earths, thorium, vanadium, zinc, and zirconium.

The independent reaction zones may be completely separated one from the other or superimposed or otherwise associated one with the other but with the outlet from the first zone communicating with the inlet to the second zone.

Having described the basic concepts of this invention, the invention will now be illustrated by the following examples, which are given by way of illustration and not by way of limitation:

EXAMPLE 1

Use is made of 2.74 liters of catalyst formed of a carrier of alumina balls having a diameter from 3 to 5 mm and an average specific surface of 1 $m^2/g$ in pores from 0.2 to 8 microns in which the carrier is impregnated with 5% by weight copper in the form of $CuCl_2 \cdot 2H_2O$ and 3% by weight potassium in the form of KCl. The catalyst is poured to form the fixed bed in a first reaction zone composed of a nickel tubular reactor having a diameter of 32 mm and a length of 3700 mm.

A second zone formed of an Inconel tubular reactor (containing 73% by weight nickel) having a diameter of 65 mm is filled over a length of 3500 mm with a catalyst formed of a carrier of alumina balls having a diameter of 3 to 6 mm with an average specific surface of 2 $m^2/g$ in pores of 0.1 to 1 micron and impregnated with 5% by weight copper in the form of $CuCl_2 \cdot 2H_2O$ and 3% by weight potassium in the form of KCl.

With the tubular reactors connected in series, a gaseous mixture of ethylene, hydrochloric acid and air is fed at a total flow rate based on ethylene of 2.7 moles per hour per liter of catalyst with the molar ratios of the reagents having the following values:

$$O_2/C_2H_4 = 0.65 \text{ and } HCl/C_2H_4 = 2.30$$

The pressure of the reactants in the inlet to the first reactor is 1.5 bars while the pressure of reactants to the second reactor is 1.2 bars.

Both reactors, which are jacketed for circulation of a heat exchange fluid, are heated to starting reaction temperature. The temperature in the warmest region of the first reactor is maintained at 350° to 360° C while the temperature in the warmest region of the second reactor is maintained at 385° to 395° C.

The following results are obtained:
At the exit of the first reaction:

| | | |
|---|---|---|
| total conversion rate of ethylene | : | 78.0% |
| conversion rate of ethylene in 1,2-dichloroethane | Xa : | 76.3% |
| conversion rate of ethylene in 1,1,2-trichloroethane | Xb : | 1.0% |
| conversion rate of ethylene in 1,1,2,2-tetrachloroethane | Xc : | 0.1% |
| conversion rate of ethylene in dichloroethylenes | : | 0.1% |
| conversion rate of ethylene in vinyl chloride | : | 0.2% |
| conversion rate of ethylene in various other products | : | 0.3% |

The yield of 1,2-dichloroethane, 1,1,2-trichloroethane and 1,1,2,2-tetrachloroethane is 77.4% based on the ethylene involved.

The proportion of $(Xb + Xc)/(Xa + Xb + Xc)$ expressed in percent is equal to 1.4.

At the exit of the second reaction zone:

| | | |
|---|---|---|
| total conversion rate of ethylene | : | 99.5% |
| total conversion rate of hydrochloric acid | : | 89.7% |
| conversion rate of ethylene in 1,2-dichloroethane | Xa : | 86% |
| conversion rate of ethylene in 1,1,2-trichloroethane | Xb : | 9.0% |
| conversion rate of ethylene in 1,1,2,2-tetrachloroethane | Xc : | 0.9% |
| conversion rate of ethylene in dichloroethylenes | : | 0.5% |
| conversion rate of ethylene in vinyl chloride | : | 2.2% |
| conversion rate of ethylene in various other products is 0.5% of which CO, $CO_2$ is 0.4% | | |

The yield of 1,2-dichloroethane and 1,1,2-trichloroethane and 1,1,2,2-tetrachloroethane is 95.9% based on the ethylene involved.

The ratio $(Xb + Xc)/(Xa + Xb + Xc)$ expressed in percent is equal to 10.1.

In a first comparative test, the catalyst carrier in the first reactor is alumina having a granular size of 3 to 5 mm with an average specific surface of 3.5 m²/g in pores of 0.1 to 2 microns and impregnated with 5% by weight copper in the form of $CuCl_2 \cdot 2H_2O$ and 3% by weight potassium in the form of KCl.

The temperature of heat exchanger fluid is raised progressively up to reaction starting. Thereafter, a hot spot develops, the temperature of which increases rapidly and goes out of control.

In spite of a rapid temperature lowering of the heat exchanger fluid to 200° C, the hot spot temperature reaches and then exceeds 550° C.

Analyses of the gaseous effluents reveal the presence of an ethylene conversion rate in carbon dioxide and in carbon monoxide above 15 molar percent resulting from the combustion of ethylene.

The feed flow rates have to be stopped immediately for security reasons without achieving stabilization of the hot spot temperature.

In a second comparative test, the catalyst carrier in the second reactor in alumina having a granular size of 3 to 6 mm diameter with an average specific surface of 0.6 m²/g in pores of 0.5 to 10 microns and impregnated with 5% by weight copper in the form of $CuCl_2 \cdot 2H_2O$ and with 3% by weight potassium in the form of KCl. The catalyst of the first reactor remains identical to that of Example 1.

Temperatures of the warm region in the first and the second reactor are 360° C and 370°–380° C, respectively.

The following results are obtained:

| | | |
|---|---|---|
| total conversion rate of ethylene | : | 99% |
| total conversion rate of hydrochloric acid | : | 86.2% |
| conversion rate of ethylene in 1,2-dichloroethane | : | 97.0% |
| conversion rate of ethylene in 1,1,2-trichloroethane | : | 1.5% |
| conversion rate of ethylene in 1,1,2,2-tetrachloroethane | : | 0.1% |
| conversion rate of ethylene in vinyl chloride | : | 0.4% |
| conversion rate of ethylene in various products | : | <0.1% |

The yield of 1,2-dichloroethane, 1,1,2-trichloroethane and 1,1,2,2-tetrachloroethane is 98.6% based on the involved ethylene, while the proportion $(Xb + Xc)/(Xa + Xb + Xc)$ expressed in percent is only 1.7, which explains the relatively very low proportions of 1,1,2-trichloroethane and 1,1,2,2-tetrachloroethane obtained and is consequently contrary to the object of this invention.

In a third comparative test, the operating conditions of Example 1 are renewed, except that the temperature in the second reactor is raised to 445°–455° C.

The following results or obtained:

| | | |
|---|---|---|
| total conversion rate of ethylene | : | 96% |
| total conversion rate of hydrochloric acid | : | 79.6% |
| conversion rate of ethylene in 1,2-dichloroethane | : | 49% |
| conversion rate of ethylene in 1,1,2-trichloroethane | : | 13% |
| conversion rate of ethylene in 1,1,2,2-tetrachloroethane | : | 0.5% |
| conversion rate of ethylene in vinyl chloride | : | 21% |
| conversion rate of ethylene in CO and $CO_2$ | : | 1% |
| conversion rate of ethylene in various products | : | 1% |

Although the ratio $(Xb + Xc)/(Xa + Xb + Xc)$ expressed in percent is equal to a high value of 21.6, the conversion rate of ethylene in 1,2-dichloroethane, 1,1,2-trichloroethane and 1,1,2,2-tetrachloroethane is only 62.5%.

In a fourth comparative test, operating conditions of Example 1 are repeated, but the feed ratio $HCl/C_2H_4$ is lowered to the value of 1.78.

The warm region temperature in the second reactor is maintained at a temperature of 380°–390° C. The following results are then obtained:

| | | |
|---|---|---|
| total conversion of ethylene | : | 88.4% |
| total conversion rate of hydrochloric acid | : | 99.3% |
| conversion rate of ethylene in 1,2-dichloroethane | : | 82.5% |
| conversion rate of ethylene in 1,1,2-trichloroethane | : | 2.5% |
| conversion rate of ethylene in 1,1,2,2-tetrachloroethane | : | 0.1% |
| conversion rate of ethylene in vinyl chloride | : | 2.5% |
| conversion rate of ethylene in various products | : | 0.8% |

The yield of 1,2-dichloroethane, 1,1,2-trichloroethane and 1,1,2,2-tetrachloroethane is a relatively low value of 85.1% based on the ethylene, as well as the ratio $(Xb + Xc)/(Xa + Xb + Xc)$ expressed in percent which is only 3.1.

EXAMPLE II

The experimental conditions of Example I are renewed, but by applying an alternate method which consists in introducing directly 32 molar percent of the total air flow into the second reactor with a corresponding amount being deducted from the feed to the first reactor.

The following results are observed:

At the exit of first reaction zone:

| | | |
|---|---|---|
| total conversion rate of ethylene | : | 70.1% |
| conversion rate of ethylene in 1,2-dichloroethane | Xa : | 68.7% |
| conversion rate of ethylene in 1,1,2-trichloroethane | Xb : | 0.8% |
| conversion rate of ethylene in 1,1,2,2-tetrachloroethane | Xc : | 0.1% |

| | | |
|---|---|---|
| conversion rate of ethylene in dichloro-ethylenes | : | 0.1% |
| conversion rate of ethylene in vinyl choride | : | 0.1% |
| conversion rate of ethylene in various products | : | 0.3% |

The yield of 1,2-dichloroethane, 1,1,2-trichloroethane and 1,1,2,2-tetrachloroethane is 69.6% based on the involved ethylene.

The ratio $(Xb + Xc)/(Xa + Xb + Xc)$ expressed in percent is equal to 1.3.

At the exit of second reaction zone:

| | | |
|---|---|---|
| total conversion rate of ethylene | : | 99.5% |
| total conversion rate of hydrochloric acid | : | 92.7% |
| conversion rate of ethylene in 1,2-dichloro-ethane | Xa : | 80.3% |
| conversion rate of ethylene in 1,1,2-tri-chloroethane | Xb : | 12% |
| conversion rate of ethylene in 1,1,2,2-tetrachloroethane Xc : | | 2.7% |
| conversion rate of ethylene in vinyl chloride | : | 2.1% |
| conversion rate of ethylene in dichloro-ethylenes | : | 1.7% |
| conversion rate of ethylene in combustion products | : | 0.3% |
| conversion rate of ethylene in various products | : | 0.4% |

The yield of 1,2-dichloroethane, 1,1,2-trichloroethane, 1,1,2,2-tetrachloroethane based on the ethylene is 95.0%.

The ratio $(Xb + Xc)/(Xa + Xb + Xc)$ expressed in percent is 15.5.

It can be seen that the direct introduction of part of the total air flow into the second reactor provides a very marked relative increase in 1,1,2-trichoroethane and 1,1,2,2-tetrachloroethane in the product.

EXAMPLE III

The method of Example I is followed except that the catalyst carrier in the first reactor is impregnated with 5% by weight copper, 5% by weight potassium and 2% by weight iron in the form of their corresponding chlorides, the temperature in the warm region being maintained at 340° C in this reactor.

The results of Example I are obtained.

EXAMPLE IV

The operating conditions of Example I are followed except that the catalyst carrier in the second reactor is impregnated with 5% by weight copper, 5% by weight potassium and 2% by weight iron, in the form of their chlorides and the temperature in the warm region is maintained at 360° to 370° C in the second reactor.

The same results are obtained as in Example I.

EXAMPLE V

A catalyst, the carrier of which is alumina, having an average specific surface of 0.9 m²/g in pores from 0.2 to 8 microns in the form of balls having a diameter of 2 to 5 mm, is loaded in a first nickel tubular reactor having an internal diameter of 32 mm. The balls are impregnated with a solution of cupric chloride and potassium chloride. The weight ratios $Cu/Al_2O_3$ and $K/Al_2O_3$, expressed in percent by weight, are respectively 5 and 3.

A catalyst, the carrier of which is alumina, having an average specific surface of 1.4 m²/g in pores from 0.1 to 5 microns, the catalytic agent being the same as in the first reactor, is loaded in a second tubular reactor connected to the first, having an internal diameter equal to 65 mm.

The three reagents: ethylene, air and hydrochloric acid are mixed before being admitted in the first reactor. They are introduced in the first reactor at a temperature of 150° C and under an absolute pressure of 4.3 bars at the inlet of this reactor, with pressure at the inlet of the second reactor being raised to 4 absolute bars.

The total ethylene flow rate is 2.3 moles per hour per liter catalyst with the materials being present in the molar ratios of $HCl/C_2H_4 = 2.30$ and $O_2/C_2H_4 = 0.60$.

When normal running conditions are reached in each of the reactors, a warm region is observed in which the temperatures are respectively from 357° to 367° C for the first reactor and from 370° to 380° C for the second reactor.

Under these conditions, a total ethylene conversion rate of 99.7% and a total hydrochloric acid conversion rate of 91% are obtained.

If the transformation rates of ethylene is 1,2-dichloroethane, 1,1,2-trichloroethane and 1,1,2,2-tetrachloroethane are respectively designated by Xa, Xb and Xc, there is obtained:

| | |
|---|---|
| Xa = | 85.0% |
| Xb = | 7.0% |
| Xc = | 3.5% |

The other reaction products are the following:

| | |
|---|---|
| conversion rate of ethylene in ethyl chloride | 0.5% |
| conversion rate of ethylene in vinyl chloride | 1.7% |
| conversion rate of ethylene in trichloroethylene | 0.2% |
| conversion rate of ethylene in dichloroethylenes | 1.4% |

0.4% combustion products and 0.1% various other products are obtained.

It will be observed that the process leads to a total ethylene conversion rate of 95.5% in 1,2-dichloroethane, 1,1,2-trichloroethane and 1,1,2,2-tetrachloroethane.

The ratio $(Xb + Xc)/(Xa + Xb + Xc)$ expressed in percent is 11.0.

If the warm region temperature of the second reactor is raised to 388°–398° C, all other conditions remaining unchanged, the following results are obtained:

| | | |
|---|---|---|
| total conversion rate of ethylene | : | 99.8% |
| total conversion rate of hydrochloric acid | : | 93.2% |
| conversion rate of ethylene in 1,2-dichloro-ethane | Xa : | 83.2% |
| conversion rate of ethylene in 1,1,2-tri-chloroethane | Xb : | 9% |
| conversion rate of ethylene in 1,1,2,2-tetrachloroethane | Xc : | 3% |
| conversion rate of ethylene in vinyl chloride | : | 1.8% |
| conversion rate of ethylene in trichloro-ethylene | : | 0.2% |
| conversion rate of ethylene in dichloro-ethylenes | : | 1.9% |

The conversion rate of ethylene in combustion products is 0.6% and 0.1% in various products.

The yield of ethylene in 1,2-dichloroethane, 1,1,2-trichloroethane, 1,1,2,2-tetrachloroethane is 95.2%.

The ratio $(Xb + Xc)/(Xa + Xb + Xc)$ expressed in percent is equal to 12.6.

When operating under pressure, the difference between the average specific surface of the carriers of first and second catalytic zones may be reduced more than in the case when operating under a pressure close to atmospheric pressure.

EXAMPLE VI

A catalyst, the carrier of which is alumina, having an average specific surface equal to 0.9 m²/g in pores from 0.2 to 8 microns in the form of balls having a diameter of 4 to 7 mm impregnated with a solution so as to fix 5% by weight copper and 3% by weight potassium in the form of their chlorides, is loaded in the same reactor system as that of Example V.

A catalyst, the carrier of which is alumina balls having a granular size from 4 to 7 mm and with an average specific surface of 1.4 m²/g in pores from 0.1 to 5 microns and impregnated the same as previously, is introduced in the second reactor.

The total flow rate of ethylene admitted is 6 moles per hour per liter catalyst with the reagent present in the molar ratio of $HCl/C_2H_4 = 2.30$ and $O_2/C_2H_4 = 0.65$.

The pressure of reagents at the inlet of the first reactor is maintained at 7.5 absolute bars and the pressure at the inlet of the second reactor is maintained at 6.8 absolute bars.

A warm region of 350°-360° C is observed in first reactor and a warm region of 370°-380° C in the second reactor.

The following results are obtained:

| | | |
|---|---|---|
| total conversion rate of ethylene | Xg : | 99.2% |
| total conversion rate of hydrochloric acid | Yg : | 93.5% |
| conversion rate of ethylene in 1,2-dichloroethane | Xa : | 83.4% |
| conversion rate of ethylene in 1,1,2-trichloroethane Xb : | | 10% |
| conversion rate of ethylene in 1,1,2,2-tetrachloroethane | Xc : | 4% |
| conversion rate of ethylene in vinyl chloride | : | 0.6% |
| conversion rate of ethylene in dichloroethylenes | : | 0.6% |
| conversion rate of ethylene in trichloroethylene | : | 0.2% |
| conversion rate of ethylene in combustion products | : | 0.3% |
| conversion rate of ethylene in various products | : | 0.1% |

The yield of ethylene in 1,2-dichloroethane, 1,1,2-trichloroethane and 1,1,2,2-tetrachloroethane is 97.4%.

It is observed that the productivity is sharply improved by the use of pressure.

The results obtained remain excellent, this being explained by the fact that the warmest regions in both reactors are more extended than when operating at a lower pressure.

The ratio $(Xb + Xc)/(Xa + Xb + Xc)$ expressed in percent is 14.4.

EXAMPLES VII and VIII

The same reactors and the same beds of catalysts are used as that described in Example V. Two runs are effected in which the ratios of reagents $HCl/C_2H_4$ and $O_2/C_2H_4$ are varied, the pressure at the inlet of the first reactor being 4.5 absolute bars and the pressure at the inlet of the second reactor being 4 absolute bars.

The total feed flow rate of ethylene is 3 moles per hour per liter of catalyst.

The warmest region in the first reactor is established at 335°-345° C and at 349°-359° C in the second reactor.

The results are stated in the following table:

| | EXAMPLE VII | | | EXAMPLE VIII | | |
|---|---|---|---|---|---|---|
| | At inlet of the first reactor | At exit of the first reactor | At exit of the second reactor | At inlet of the first reactor | At exit of the first reactor | At exit of the second reactor |
| HCl/C₂H₄ | 2.40 | — | — | 2.60 | — | — |
| O₂/C₂H₄ | 0.60 | — | — | 0.70 | — | — |
| XG | — | 69.3 | 98.6 | — | 70.1 | 99.2 |
| YG | — | 55 | 90.2 | — | 59 | 85 |
| Xa | — | 65.7 | 79.6 | — | 64.2 | 75 |
| Xb | — | 0.7 | 10.5 | — | 1.2 | 14 |
| Xc | — | 0 | 2.3 | — | 0.4 | 4 |
| Xa+Xb+Xc | — | 66.4 | 92.4 | — | 65.8 | 93 |
| 100(Xb+Xc)/(Xa+Xb+Xc) | — | 1.05 | 13.8 | — | 2.4 | 19.3 |

XG : total conversion rate of ethylene
YG : total conversion rate of hydrochloric acid
Xa : conversion rate of ethylene in 1,2-dichloroethane
Xb : conversion rate of ethylene in 1,1,2-trichloroethane
Xc : conversion rate of ethylene in 1,1,2,2-tetrachloroethane Both examples show that with a single reactor, i.e. with a single or first catalytic zone essentially only 1,2-dichloroethane is obtained, whereas the process of this invention permits the simultaneous production of considerable proportions of 1,1,2-trichloroethane and substantial proportions of 1,1,2,2-tetrachloroethane which are respectively 11.4% and 15% by weight 1,1,2-trichloroethane and 2.4% and 4.3% by weight 1,1,2,2-tetrachloroethane based on the entire mixture of 1,2-dichloroethane, 1,1,2-trichloroethane and 1,1,2,2-tetrachloroethane.

EXAMPLE IX

A first reaction zone composed of a next of 30 steel tubes having an internal diameter of 30 mm and a length of 4 m are connected in series with a second reaction zone composed of another nest of 13 steel tubes having an internal diameter of 50 mm.

Both reaction zones are loaded with a catalyst composed of a carrier of alumina balls having a diameter from 4 to 7 mm with an average specific surface of 0.6 m²/g in pores from 0.5 to 10 microns and impregnated with 5.9% by weight copper in the form of $CuCl_2 \cdot 2H_2O$ and with 4.4% by weight potassium in the form of KCl.

The total volume of catalyst is 164 liters.

At the inlet of the first nest of tubes, a gaseous mixture of ethylene, hydrochloric acid and air is introduced in which the total flow rate of ethylene is 3.3 moles per hour per liter of catalyst with the other ingredients having the feed molar ratio of $O_2/C_2H_4 = 0.75$ and $HCl/C_2H_4 = 2.19$.

The pressure of reagents at the inlet of the first nest of tubes is 4 absolute bars and that at the inlet of the second nest of tubes is 3.3 absolute bars.

Both systems of nests of tubes are jacketed for circulation of a heat exchanger fluid so that the maximal temperature if the first nest of tubes is 355°-365° C and the maximal temperature of the second nest of tubes is 365°-375° C.

Under these conditions, the following results are obtained:

| | | |
|---|---|---|
| total conversion rate of ethylene | : | 97% |
| total conversion rate of hydrochloric acid | : | 92% |
| conversion rate of ethylene in 1,2-dichloroethane | Xa : | 85% |
| conversion rate of ethylene in 1,1,2-trichloroethane | Xb : | 8% |
| conversion rate of ethylene in 1,1,2,2-tetrachloroethane | Xc : | 1% |
| conversion rate of ethylene in dichloroethylenes plus vinyl choride | : | 1.5% |
| conversion rate of ethylene in combustion products ($CO + CO_2$) | : | 1.5% |

The yield of 1,2-dichloroethane, 1,1,2-trichloroethane and 1,1,2,2-tetrachloroethane is 94% based on the involved ethylene.

The ratio $(Xb + Xc)/(Xa + Xb + Xc)$ expressed in percent is 9.6.

It will be apparent from the foregoing that there is provided a new and improved fixed bed catalytic system for oxychlorination of ethylene to produce a product containing significant amounts of 1,1,2-trichloroethane and 1,1,2,2-tetrachoroethane in addition to 1,2-dichloroethane.

It will be understood that changes may be made in the details of formulation and operation without departing from the spirit of the invention, especially as defined in the following claims.

We claim:

1. The process for the oxychlorination of ethylene to produce a product stream of 1,2-dichloroethane, 1,1,2-trichloroethane and 1,1,2,2-tetrachloroethane in which at least 8 mole percent of the ethylene is converted to 1,1,2-trichloroethane and 1,1,2,2-tetrachloroethane, comprising passing a mixture of an oxygen containing gas, HCl and ethylene in which the mole ratio of $HCl/C_2H_4$ is within the range of 1.8 to 3.0 and the mole ratio of $O_2/C_2H_4$ is within the range of 0.5 and 1.5 through a first reaction zone formed of one or more tubular zones containing a fixed bed oxychlorination catalyst on a carrier at a temperature of 250° to 400° C and passing the effluent from the first reaction zone to a second reaction zone formed of one or more tubular zones containing a fixed bed oxychlorination catalyst on a carrier at a temperature within the range of 255° to 410° C, with the ratio of the diameters of each of the tubular zones of the second reaction zone to the diameters of each of the tubular zones of the first reaction zone being greater than 1 and up to 3, and the temperatuare in the second reaction zone being 5° to 50° C higher than the temperature of the first reaction zone, and the average specific surface area of the carrier in the second reaction zone being at least 10% greater than the average specific surface area of the carrier in the first reaction zone, with the average specific surface area of the carrier in the first zone being less than 3 $m^2/g$ and the average specific surface area of the carrier in the second zone being less than 10 $m^2/g$.

2. The process as claimed in claim 1 wherein the carrier in the first reaction zone has a surface area of less than 1 $m^2/g$ and the carrier in the second reaction zone has a surface area of less than 4 $m^2/g$.

3. The process as claimed in claim 1 in which the gaseous reactants in the first zone are heated to a temperature within the range of 280° to 370° C and in which the effluent from the first zone is heated to a temperature within the range of 285° to 400° C during passage through the second zone.

4. The process as claimed in claim 1 in which the total molar feed ratio of $HCl/C_2H_4$ is maintained within the range of 2.1 to 2.5 and the total molar feed ratio of $O_2/C_2H_4$ is maintained with the range of 0.6 to 0.8.

5. The process as claimed in claim 1 in which the reactants are introduced at the feed rate based upon ethylene of 2 to 3 moles of ethylene per hour per liter of catalyst.

6. The process as claimed in claim 1 in which a fraction of up to 60 molar percent of at least one of the reactants is withheld from passage with the remainder through the first catalytic reaction zone and in which the portion withheld is added to the effluent from the first zone for passage therewith through the second catalytic reaction zone.

7. The process as claimed in claim 1 in which the conversion, based upon the conversion of ethylene, is maintained within the range of 40 to 80% during passage through the first catalytic reaction zone.

8. The process as claimed in claim 1 in which the pressure in the reaction zones is within the range of 1 to 10 absolute bars.

9. The process as claimed in claim 1 in which the pressure in the reaction zones is within the range of 2 to 7 absolute bars.

* * * * *

UNITED STATES PATENT OFFICE
CERTIFICATE OF CORRECTION

Patent No. 3,992,463              Dated November 16, 1976

Inventor(s) Gerard BENAROYA et al.

It is certified that error appears in the above-identified patent and that said Letters Patent are hereby corrected as shown below:

In column 8, line 35, "0.5%" should be -- 0.4% --.

Signed and Sealed this

Twenty-second Day of February 1977

[SEAL]

Attest:

RUTH C. MASON
*Attesting Officer*

C. MARSHALL DANN
*Commissioner of Patents and Trademarks*